(12) United States Patent
Fukasawa et al.

(10) Patent No.: US 9,498,393 B2
(45) Date of Patent: Nov. 22, 2016

(54) WEARING ARTICLE

(71) Applicant: UNICHARM CORPORATION, Shikokuchuo-shi, Eime (JP)

(72) Inventors: Jun Fukasawa, Kanonji (JP); Tatsuya Hashimoto, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 0 days.

(21) Appl. No.: 14/399,465

(22) PCT Filed: Jun. 20, 2013

(86) PCT No.: PCT/JP2013/003839
§ 371 (c)(1),
(2) Date: Nov. 6, 2014

(87) PCT Pub. No.: WO2014/002439
PCT Pub. Date: Jan. 3, 2014

(65) Prior Publication Data
US 2015/0148768 A1  May 28, 2015

(30) Foreign Application Priority Data
Jun. 26, 2012 (JP) ................. 2012-143515

(51) Int. Cl.
*A61F 13/49* (2006.01)
*A61F 13/494* (2006.01)

(52) U.S. Cl.
CPC .... *A61F 13/49017* (2013.01); *A61F 13/49011* (2013.01); *A61F 13/49012* (2013.01); *A61F 13/49061* (2013.01); *A61F 13/49466* (2013.01)

(58) Field of Classification Search
CPC .................. A61F 13/49466; A61F 13/49061
See application file for complete search history.

(56) References Cited

U.S. PATENT DOCUMENTS 6,425,889 B1 * 7/2002 Kitaoka ............ A61F 13/49466
604/369
7,901,393 B2   3/2011 Matsuda et al.
(Continued)

FOREIGN PATENT DOCUMENTS

JP   2008-508082 A   3/2008
JP   2011-025006 A   2/2011
(Continued)

OTHER PUBLICATIONS

International Search Report mailed Aug. 13, 2013 in International Application No. PCT/JP2013/003839 filed Jun. 20, 2013.
(Continued)

*Primary Examiner* — Susan Su
(74) *Attorney, Agent, or Firm* — Hauptman Ham, LLP

(57) ABSTRACT

A diaper includes front and rear waist panels respectively defining front and rear waist regions, a crotch panel defining a crotch region, and an absorbent structure extending in a longitudinal direction. The crotch panel has a base sheet and a pair of leg sheets attached to both lateral edge portions of the base sheet. In vicinities of front and rear end portions of the crotch panel, first joint regions extending in a transverse direction from the base sheet beyond outer lateral edge portions of the respective leg sheets are formed. Through these joint regions, the crotch panel is joined to the front and rear waist panels. Cover sheets adapted to cover the front and rear end portions are joined to an interior crotch sheet of the crotch panel through second joint regions. The cover sheets extend outwardly in the transverse direction beyond the first joint regions.

13 Claims, 6 Drawing Sheets

(56) References Cited

U.S. PATENT DOCUMENTS

| | | | | |
|---|---|---|---|---|
| 2009/0326504 A1* | 12/2009 | Kaneda | ............ | A61F 13/49011 604/385.23 |
| 2011/0077609 A1* | 3/2011 | Kuwano | ........... | A61F 13/49011 604/385.01 |
| 2011/0098668 A1* | 4/2011 | Thorson | ............ | A61F 13/49012 604/385.25 |
| 2012/0022482 A1* | 1/2012 | Nakajima | ......... | A61F 13/49466 604/385.3 |
| 2012/0095429 A1 | 4/2012 | Kobayashi et al. | | |
| 2012/0191057 A1* | 7/2012 | Takino | .............. | A61F 13/49011 604/385.29 |
| 2012/0226254 A1* | 9/2012 | Takino | .................. | A61F 13/496 604/385.3 |
| 2012/0226255 A1* | 9/2012 | Takeuchi | .......... | A61F 13/49011 604/385.3 |
| 2012/0271266 A1* | 10/2012 | Sasayama | ......... | A61F 13/15593 604/385.24 |
| 2012/0278975 A1* | 11/2012 | Yamashita | ........ | A61F 13/49466 2/400 |
| 2013/0012906 A1 | 1/2013 | Takino | | |
| 2013/0172841 A1* | 7/2013 | Ichikawa | .............. | A61F 13/496 604/366 |
| 2013/0184666 A1* | 7/2013 | Sasayama | ......... | A61F 13/49011 604/378 |
| 2013/0211366 A1* | 8/2013 | Gassner | ............ | A61F 13/49011 604/385.29 |
| 2013/0304011 A1* | 11/2013 | Sasayama | ......... | A61F 13/49017 604/370 |

FOREIGN PATENT DOCUMENTS

| | | |
|---|---|---|
| JP | 2011-136032 A | 7/2011 |
| JP | 2011-156341 A | 8/2011 |
| JP | 2012-071060 A | 4/2012 |
| WO | 2011/040046 A1 | 4/2011 |
| WO | 2011/125908 A1 | 10/2011 |
| WO | 2012/029295 A1 | 3/2012 |

OTHER PUBLICATIONS

Written Opinion of the International Searching Authority mailed Aug. 13, 2013 in corresponding International Application No. PCT/JP2013/003839 filed Jun. 20, 2013.

Extended European Search Report dated Nov. 19, 2015, corresponding to European Patent Application No. 13810200.9.

* cited by examiner

WEARING ARTICLE

RELATED APPLICATIONS

The present application is a National Phase of Application No. PCT/JP2013/003839, filed Jun. 20, 2013, which claims priority to Japanese Application No. 2012-143515, filed Jun. 26, 2012.

WEARING ARTICLE

1. Technical Field

The present disclosure relates to wearing articles, for example, pants-type disposable diapers, disposable toilet-training pants and disposable incontinent pants.

2. Background

Wearing articles having a crotch region joined to front and rear waist regions are known. For example, JP 2008-508082 A (PTL 1) discloses a pull-on diaper in which front and rear end regions of a main absorbent body defining a crotch region are joined to an annular elastic belt defining front and rear waist regions.

CITATION LIST

Patent Literature

{PTL 1}
JP 2008-508082 A

SUMMARY

Technical Problem

In the wearing article disclosed in PTL 1, when front and rear end regions of the main absorbent body are attached to the annular elastic belt with an adhesive, the adhesive is not distributed to the vicinity of the end regions and the lateral edge regions thereof to leave dry edges in order to prevent the adhesive from running off from the main absorbent body. However, the inventor(s) has noted that the dry edge formed in this manner facilitates particularly the lateral edge regions of the main absorbent body to be spaced away from the annular elastic belt and eventually to be curled inwardly of the wearing article during use thereof. If the lateral edge regions are curled inwardly of the wearing article, the fit of the wearing article to the wearers skin will be deteriorated and eventually problems such as leakage of body exudates may be induced.

Solution to Problem

Some embodiments of the present invention relate to a wearing article having a longitudinal direction in parallel to a longitudinal axis, a transverse direction in parallel to a transverse axis, and opposite skin-facing surface and non-skin-facing surface. The wearing article includes front and rear waist panels respectively defining front and rear waist regions, a crotch panel defining a crotch region, and an absorbent structure lying at least on the crotch panel and extending in the longitudinal direction.

The crotch panel has front and rear end portions extending in the transverse direction and lateral edge portions extending in the longitudinal direction. The front and rear end portions are joined to the front and rear waist panels through first joint regions, and at least the first joint region in the rear waist panel overlaps the lateral edge portions of the crotch panel. A cover sheet covering the rear end portion and the corresponding first joint region in the crotch panel is attached to the rear waist panel.

BRIEF DESCRIPTION OF DRAWINGS

The drawings illustrate specific embodiments of the present invention including optional and preferred embodiments as well as essential features of the invention.

DESCRIPTION OF EMBODIMENTS

The embodiments described below relate to a diaper as illustrated in FIGS. 1 through 6, including both optional and preferred features as well as those features which are essential features of the present invention.

Figure 1:
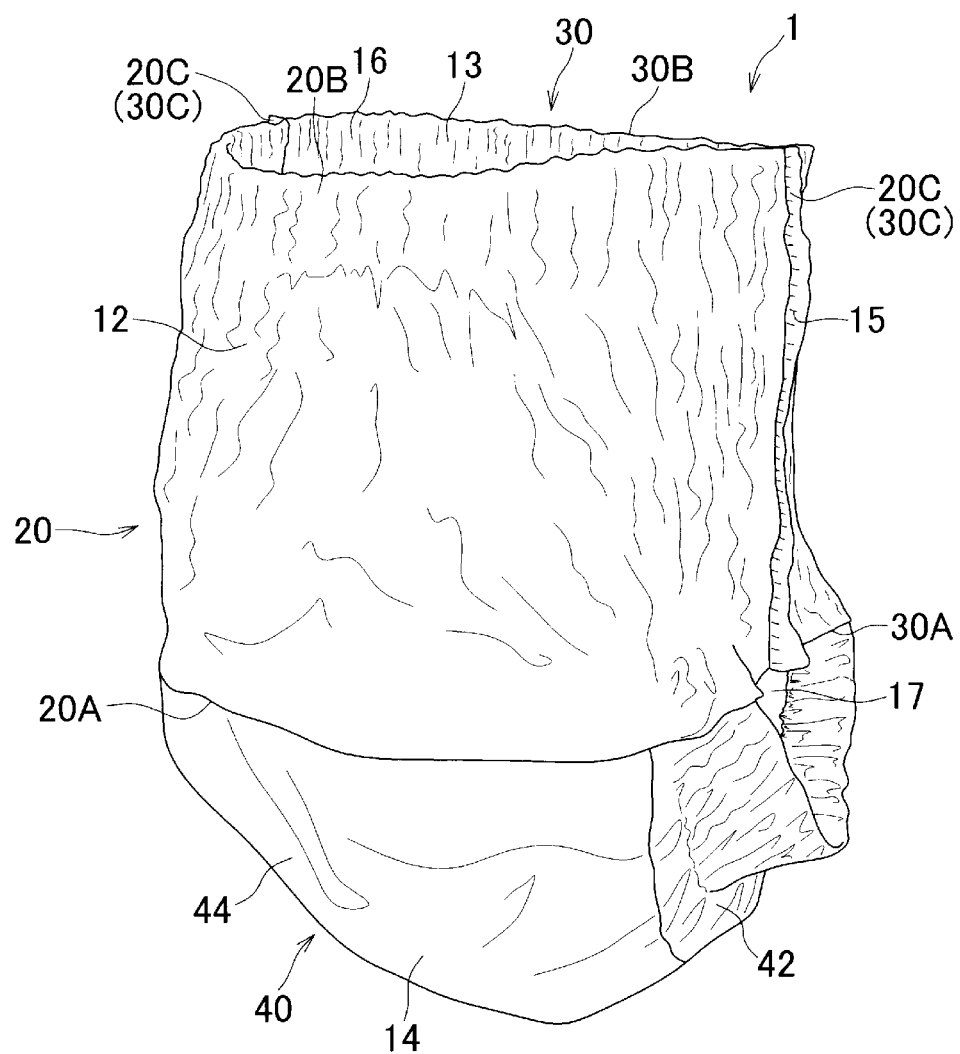
FIG. 1 is a perspective view of a disposable diaper as an example of a wearing article according to some embodiments of the present invention.
Figure 2:
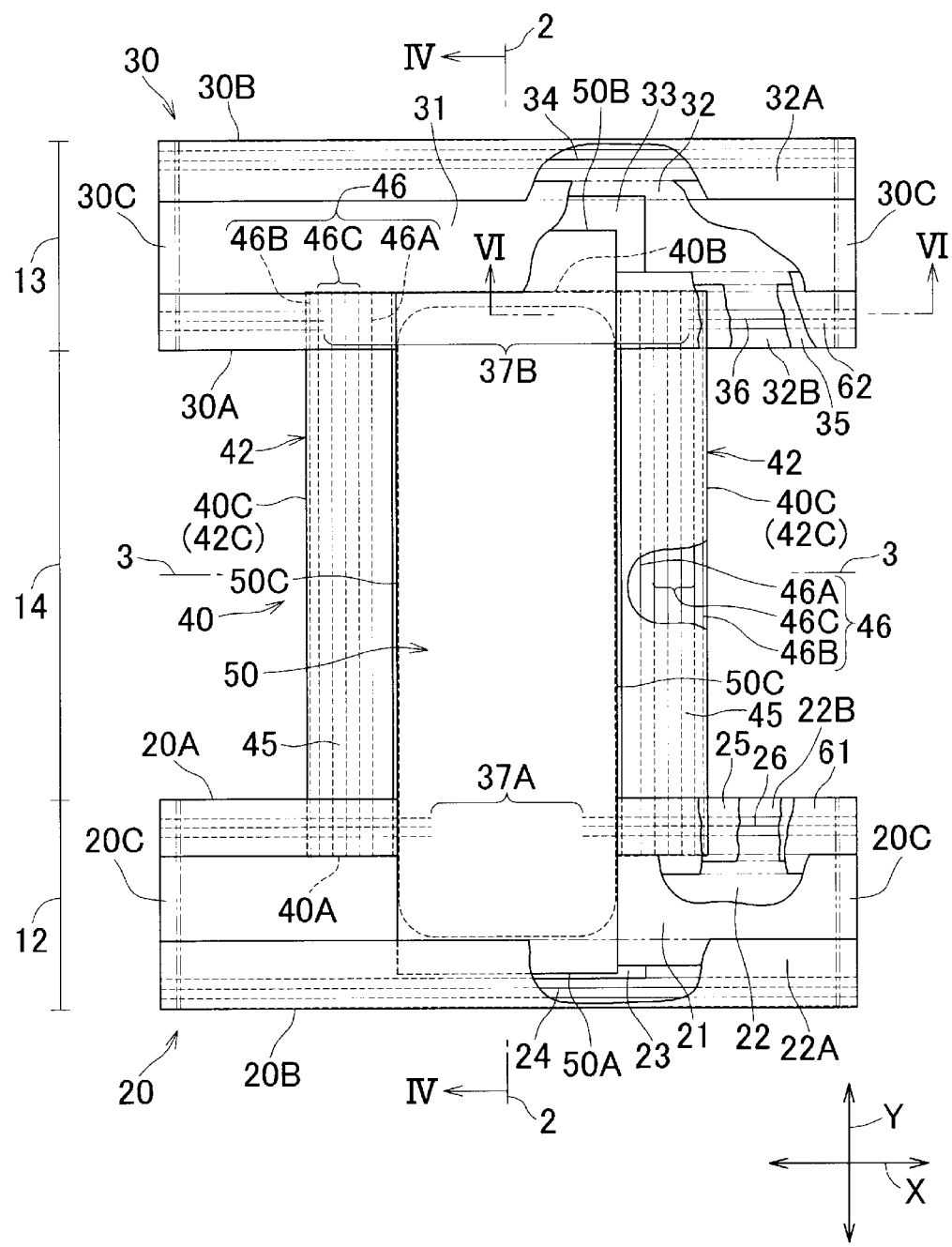
FIG. 2 is a partially cutaway developed plan view with respective elastics in a state of the maximum elongation in a longitudinal direction as well as in a transverse direction.

Referring to FIGS. 1 and 2, a diaper 1 as an example of the wearing article according to some embodiments of the present invention has a longitudinal direction Y in parallel to a longitudinal axis 2-2, a transverse direction X in parallel to a transverse axis 3-3, and opposite skin-facing surface and non-skin-facing surface. The wearing article includes a front waist region 12, a rear waist region 13, a crotch region 14 lying between the front and rear waist regions 12, 13, elastic front and rear waist panels 20, 30 respectively defining the front and rear waist regions 12, 13, a crotch panel 40 defining the crotch region 14 and attached to the respective skin-facing surfaces of the front and rear waist panels 20, 30 and an absorbent structure 50 located on the skin-facing surface of the crotch panel 40 so as to extend in the longitudinal direction Y.

The front and rear waist panels 20, 30 are respectively defined by inner ends 20A, 30A, outer ends 20B, 30B and lateral edge portions 20C, 30C. The lateral edges 20C and the lateral edges 30C may be overlapped with and joined to each other along a pair of series of seams 15 arranged at intervals in the longitudinal direction Y, for example, by a fusion-bonding technique such as a heat-embossing/debossing processing and an ultrasonic processing to form an annular elastic waist panel, thereby defining a waist-opening 16 and a pair of leg-openings 17.

Figure 3:
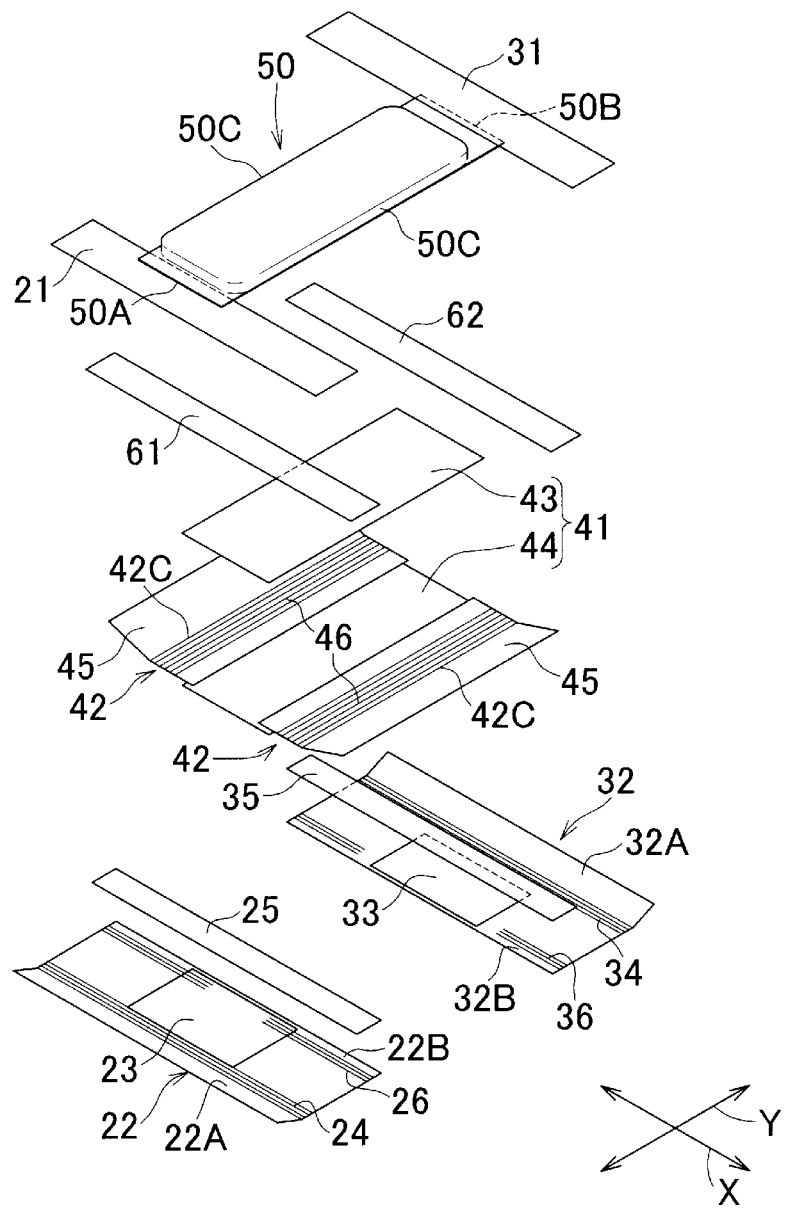
FIG. 3 is an exploded perspective view of the diaper.
Figure 4:
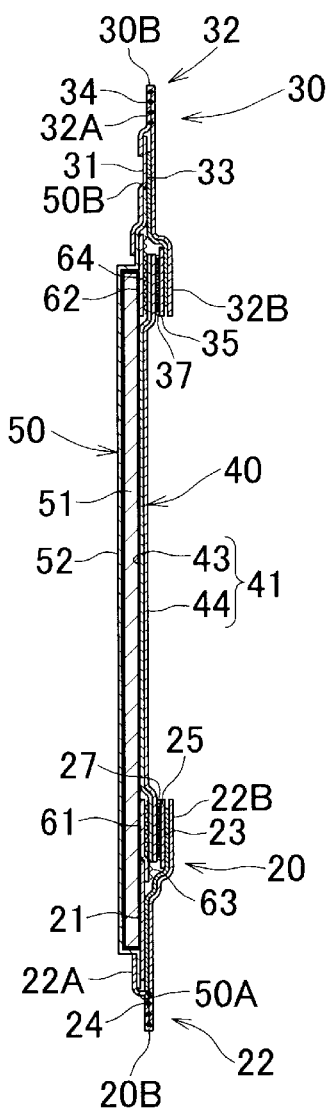
FIG. 4 is a sectional view taken along line IV-IV in FIG. 2.

Referring to FIGS. 2 through 4, in at least one embodiment the front and rear waist panels 20, 30, respectively, may have interior waist sheets 21, 31 lying on the side of the skin-facing surface and exterior waist sheets 22, 32 lying on the side of the non-skin-facing surface. The exterior waist sheets 22, 32 have a width dimension in the longitudinal direction Y larger than those of the interior waist sheets 21, 31 and extend outwardly in the longitudinal direction Y beyond inner and outer ends of the interior waist sheets 21, 31. The interior waist sheets 21, 31 and the exterior waist sheets 22, 32 are joined to each other for example with a hot melt adhesive distributed to an interior surface of at least one of the respectively associated inner and exterior waist sheets or by a fusion-bonding technique.

Materials which may be used as the exterior waist sheets 22, 32 include, for example, an SMS (spunbonded/meltblown/spunbonded) fibrous nonwoven fabric, a spun bonded fibrous nonwoven fabric, an air-through fibrous nonwoven fabric, a plastic sheet or a laminated sheet of any one of these fibrous nonwoven fabrics and the plastic sheet, for example each having a mass per unit area in a range of about 10 to about 30 g/m$^2$.

Materials which may be used as the interior waist sheets 21, 31 include elastic fibrous nonwoven fabrics such as, for example, a spun bonded fibrous nonwoven fabric, a melt blown fibrous nonwoven fabric, a heat-rolled fibrous nonwoven fabric, an SMS fibrous nonwoven fabric, an air-laid fibrous nonwoven fabric and an air-through fibrous nonwoven fabric. Such elastic fibrous nonwoven fabrics may be used solely or in combination to form the interior waist sheets 21, 31. The elastic nonwoven fabrics may be formed from an elastomeric resin such as a polyethylene-based or polyurethane-based elastomeric resin or from thermoplastic resin such as polyethylene-, polypropylene-, polyester- or acryl-based thermoplastic resin. As material of the interior waist sheets 21, 31, an inelastic fibrous nonwoven fabric also may be used.

The exterior waist sheets 22, 32 may have folded regions 22A, 32A defined by portions of the exterior waist sheets 22, 32 extending outwardly in the longitudinal direction Y beyond the outer ends of the interior waist sheets 21, 31 and folded inwardly in the longitudinal direction Y, and extension regions 22B, 32B extending from the inner ends of the interior waist sheets 21, 31 inwardly in the longitudinal direction Y toward the transverse axis 3-3. Within the folded regions 22A, 32A, a plurality of thread, strand or string first and second waist elastics 24, 34 may be contractibly attached under tension, for example with a hot melt adhesive. The first and second waist elastics 24, 34 extend in the transverse direction X across the entire regions 22A, 32A. These first and second waist elastics 24, 34 arranged in this manner are particularly effective to keep the waist-opening 16 of the diaper 1 in close contact with the wearer's body and to prevent body exudates such as urine from leaking beyond the waist opening periphery.

The extension regions 22B, 32B of the exterior waist sheets 22, 32 extending from the interior waist sheets 21, 31 inwardly in the longitudinal direction Y toward the transverse axis 3-3 may be disposed with elongate reinforcing sheets 25, 35 formed for example of a fibrous nonwoven fabric and thread, strand or string third and fourth waist elastics 26, 36 may be contractibly attached under tension between the reinforcing sheets 25, 35 and the extension regions 22B, 32B, for example with a hot melt adhesive. Both the third and fourth waist elastics 26, 36 are not continuous in vicinities of the longitudinal axis 2-2, so as to form inelastic regions 37A, 37B of respective midsections of the front and rear waist regions 12, 13. As a method of forming these inelastic regions 37A, 37B, for example, the adhesive may be distributed on respective lateral portions of the exterior waist sheets 22, 32 exclusive of the respective midsections, then the third and fourth waist elastics 26, 36 continuously fed under tension onto the regions distributed with the adhesive as well as the inelastic regions 37A, 37B may be secured to the region distributed with the adhesive, and portions of the third and fourth waist elastics 26, 36 extending on the inelastic regions 37A, 37B may be cut so that respective inner ends in a length direction of the third and fourth waist elastics 26, 36 may contract (snap back).

Alternatively, portions of the third and fourth waist elastics 26, 36 predetermined to extend across the inelastic regions 37A, 37B may be inhibited from being elongated in order to form the inelastic regions 37A, 37B. It is also possible to deprive or inhibit a contractile property of the portions of the third and fourth waist elastics 26, 36 extending under tension across the inelastic regions 37A, 37B in order to form the inelastic regions 37A, 37B. The formation of the inelastic regions 37A, 37B ensures that the absorbent structure 50 located on the longitudinal axis 2-2 is prevented from getting wrinkles or creases and the contractile force of the third and fourth elastics 26, 36 ensures that the leg-openings are kept in close contact with the wearer's body so as to prevent leakage of body exudates such as urine.

As the first-fourth waist elastics, for example, elastic waist materials having a fineness in a range of about 310 to about 940 dtex and an elongation ratio in a range of 2.0 to 3.5 may be used.

Between the respective interior waist sheets 21, 31 and the respective exterior waist sheets 22, 32, graphic display films 23, 33 formed of a plastic material may be interposed so that these graphic display films may be respectively located on midsections in the transverse direction X of the front and rear waist regions 12, 13. The graphic display films 23, 33 may be printed on the surface facing the exterior waist sheets 22, 32 with graphics (not shown) or the like which are visually recognizable through the exterior waist sheets 22, 32.

The crotch panel 40 has front and rear end portions 40A, 40B extending in the transverse direction X and overlapping with the front and rear waist panels 20, 30, and lateral edge portions 40C extending in the longitudinal direction Y and may include a base sheet 41 lying in a midsection in the transverse direction X and a pair of leg sheets 42 attached to lateral edge portions of the base sheet 41. The front and rear end portions 40A, 40B may be defined by respective front and rear ends of the base sheet 41 and the leg sheets 42, respectively, and the lateral edge portions 40C may be defined by respective outer lateral edge portions 42C of the leg sheets 42. The dimension in the longitudinal direction Y of the crotch panel 40 is smaller than the dimension in the longitudinal direction Y of the absorbent structure 50 and, consequently, front and rear end portions 50A, 50B of the absorbent structure 50 may lie outboard of the front and rear end portions 40A, 40B of the crotch panel 40 in the longitudinal direction Y.

Since the dimension of the crotch panel 40 in the longitudinal direction Y may be relatively small, the interior waist sheets 21, 31 may be put in direct contact with the wearer's skin over a correspondingly larger area during use of the diaper 1. In general, the area of the crotch panel 40 will be enlarged when the dimension in the longitudinal direction Y of the crotch panel 40 is set to be relatively large, so that the areas of the crotch panel 40 overlapping with the front and rear waist panels 20, 30 may be correspondingly enlarged. In contrast, according to at least one embodiment, the interior waist sheets 21, 31 are kept in contact with the wearer's skin over a further larger area. The interior waist sheets 21, 31 formed of an elastic fibrous nonwoven fabric make it possible to keep the front and rear waist regions 12, 13 of the diaper 1 in close contact with the wearer's skin over a large area and, in addition, to improve a texture of the diaper 1.

The base sheet 41 may include an interior crotch sheet 43 and an exterior crotch sheet 44. While various types of fibrous nonwoven fabrics or plastic films may be used as material of the interior and exterior crotch sheets 43, 44, the interior crotch sheet 43 is preferably formed of a leakage barrier plastic film and the exterior crotch sheet 44 is preferably formed of a fibrous nonwoven fabric providing a texture superior to that of the plastic film in consideration that the exterior crotch sheet 44 partially constituting the exterior surface of the diaper 10. The leg sheets 42 may have respective inner lateral edges attached between the interior and exterior crotch sheets 43, 44.

Each of the leg sheets 42 may include the outer lateral edge portion 42C folded inwardly in the transverse direction X so as to form a folding portion 45, and a plurality of thread, strand or string leg elastics 46 extending in the longitudinal direction Y may be attached within a sleeve defined by the folding portion 45. Thus the leg sheets 42 are elasticized with the leg elastics 46. As the leg elastics 46, elastic materials having a fineness in a range of about 310 to about 620 dtex and an elongation ratio in a range of about 2.0 to about 3.0 may be used, and the leg elastics 46 are contractibly attached under tension within the sleeve with a hot melt adhesive. The leg elastics 46 may include an innermost leg elastic 46A closest to the longitudinal axis 2-2, i.e., lying on the innermost side in the transverse direction X, an outermost leg elastic 46B lying on the outermost side in the transverse direction X and intermediate leg elastics 46C lying between the innermost elastic 46A and the outermost elastic 46B. According to at least one embodiment, each of the innermost leg elastic 46 and the outermost leg elastic 46B is defined by a single elastic thread, and the intermediate leg elastics 46C are defined by four elastic threads. The outermost leg elastic 46B may extend across the outer lateral edge portion 42C of the associated leg sheet 42 and the outer lateral edge portion 42C may be folded inwardly along the outermost elastic 46B.

The innermost leg elastic 46A may have a tensile stress higher than that of each of the outermost leg elastic 46B and the intermediate elastics 46C. For example, an elastic thread having a fineness of about 470 dtex and an elongation ratio of about 2.45 may be used for the innermost leg elastic 46A and an elastic thread having a fineness of about 310 dtex and an elongation ratio of about 2.45 may be used for the outermost leg elastic 46B and the intermediate leg elastics 46C.

In the front waist panel 20, the third waist elastics 26 extending in the transverse direction X may intersect (or overlap) with all of the innermost leg elastics 46A, the outermost leg elastics 46B and the intermediate leg elastics 46C. Consequently, the absorbent structure 50 is kept in contact with the wearers body under a contractile force of the third waist elastics 26 and a gap, through which body exudates might leak, is unlikely to be formed between the wearer's body and the absorbent structure 50 due to movements of the wearer's thighs. In the rear waist panel 30, the fourth waist elastics 36 extending in the transverse direction X may intersect (or overlap) with respective portions of the outermost leg elastics 46B and at least one of the intermediate leg elastics 46C, but not with the remaining intermediate leg elastics 46C and the innermost elastics 46A. In consequence, in the rear waist region 13, particularly a contractile force of the elastics 46 does not work on the absorbent structure 50, and cracks and/or wrinkles potentially causing a leakage of body exudates are unlikely to be generated.

As used herein, "the leg elastics 46 intersect with the third and fourth waist elastics 26, 36" is meant that the reinforcing sheets 25, 35 respectively provided with the third and fourth waist elastics 26, 36 contractibly attached thereto under tension and the leg sheets 42 disposed with the leg elastics 46 contractibly attached thereto under tension are joined to each other and consequently an effective elongation region of the leg elastics 46 and effective elongation regions of the third and fourth waist elastics 26, 36 are substantially in a coordinating relationship.

The base sheet 41 of the crotch panel 40 is disposed on the skin-facing surface thereof with the absorbent structure 50. The absorbent structure 50 may have a longitudinally long pad-like configuration including front and rear ends 50A, 50B, lateral edges 50C, an absorbent core 51 extending in the longitudinal direction Y at least in the crotch region 14 and a bodyside liner 52 lying on an absorbent surface of the absorbent core 51, i.e., on the skin-facing surface of the absorbent core 51. The front end 50A may be attached to the interior waist sheet 21 of the front waist panel 20 with a hot melt adhesive. The rear end 50B is attached between the interior waist sheet 31 of the rear waist panel 30 and the exterior waist sheet 32, more specifically, between the interior waist sheet 31 and the reinforcing sheet 35, for example with a hot melt adhesive. An intermediate portion of the absorbent structure 50 between the front and rear ends 50A, 50B may be attached to the interior crotch sheet 43 of the crotch panel 40, for example with a hot melt adhesive. The front end 50A of the absorbent structure 50 may be attached to the skin-facing surface of the interior waist sheet 21 and, in consequence, the elasticized and relatively flexible interior waist sheet 21 comes in direct contact with the wearer's skin to improve texture. In addition, when the rear end 50B is attached between the interior waist sheet 31 and the exterior waist sheet 32, consequently, even if a voided urine diffuses from the crotch region 14 to the portion of the absorbent structure 50 lying in the rear waist region 13, it is possible to prevent body exudates from coming in direct contact with the wearers skin. The front and rear ends 50A, 50B of the absorbent structure 50 lie outboard of the front and rear ends of the respective leg sheets 42 in the longitudinal direction Y and, in other words, a dimension in the longitudinal direction Y of the respective leg sheets 42 is smaller than a dimension in the longitudinal direction Y of the absorbent structure 50.

The absorbent core 51 may have a mass per unit area in a range of about 200 to about 800 g/m$^2$ and may include the core material formed from a mixture of fluff wood pulp, superabsorbent polymer particles (SAP) and optionally contained thermal bonding staple fibers, and a liquid-permeable fibrous nonwoven fabric adapted to wrap the core material. As material of the bodyside liner 52, various types of fibrous nonwoven fabrics such as a liquid-permeable spun bonded nonwoven fabric or an SMS nonwoven fabric each having a mass per unit area in a range of about 10 to 30 g/m$^2$ may be used, for example.

Figure 5:
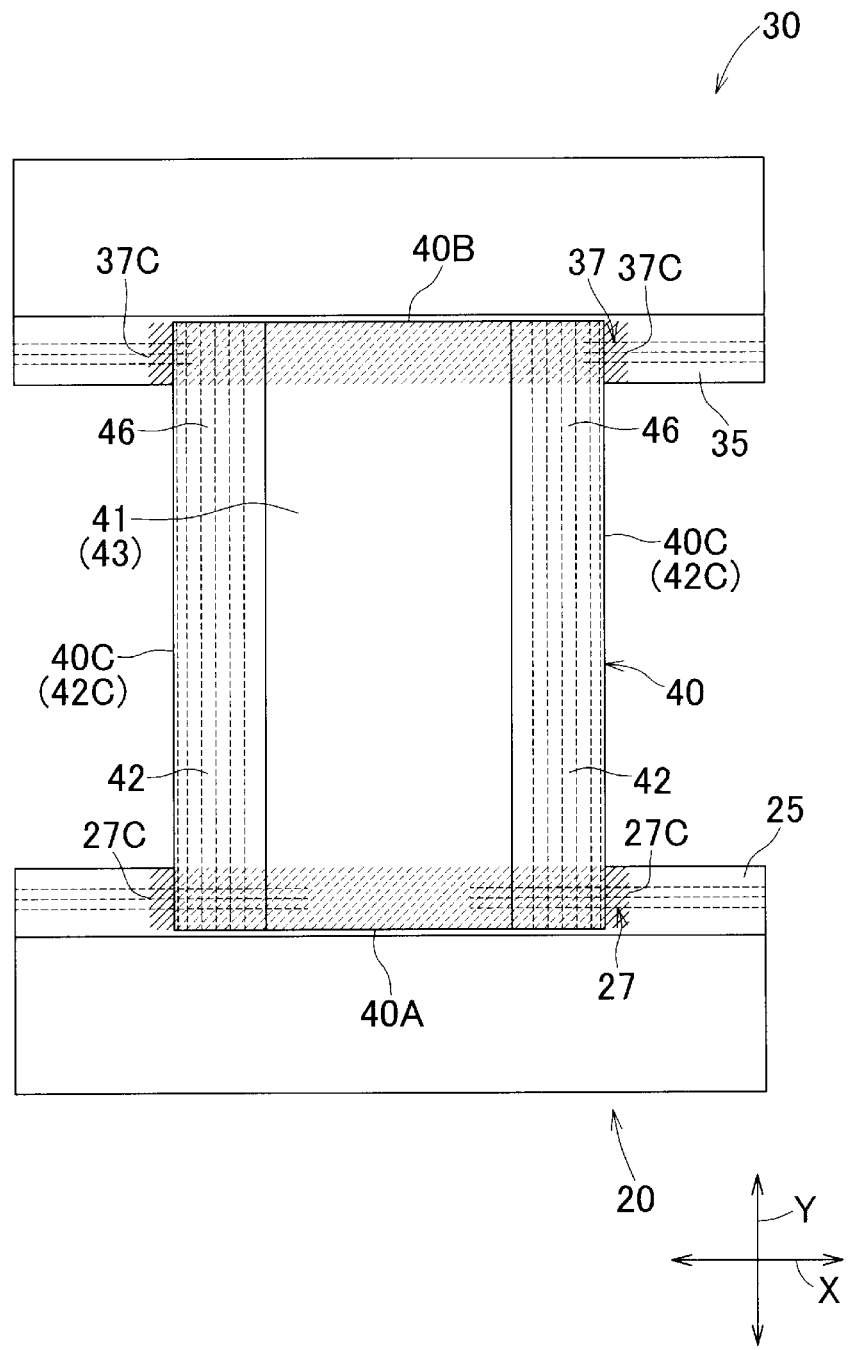
FIG. 5 is a view similar to FIG. 2, illustrating a first joint region.

Referring to FIG. 5, in portions of the front and rear ends 40A, 40B of the crotch panel 40, first joint regions 27, 37 extend in the transverse direction X from the base sheet 41 to the leg sheets 42 and the crotch panel 40 are joined to the front and rear waist panels 20, 30 through the first joint regions 27, 37. The first joint regions 27, 37 may be formed of for example a hot melt adhesive distributed on the reinforcing sheets 25, 35, and lateral edge portions 27C, 37C of the first joint regions 27, 37 extend outwardly in the transverse direction X beyond the outer lateral edge portions 42C of the respective leg sheets 42. In consequence, portions of the first joint regions 27, 37 overlap with the lateral edge portions 42C which are reliably joined to the front and rear waist panels 20, 30.

Figure 6:
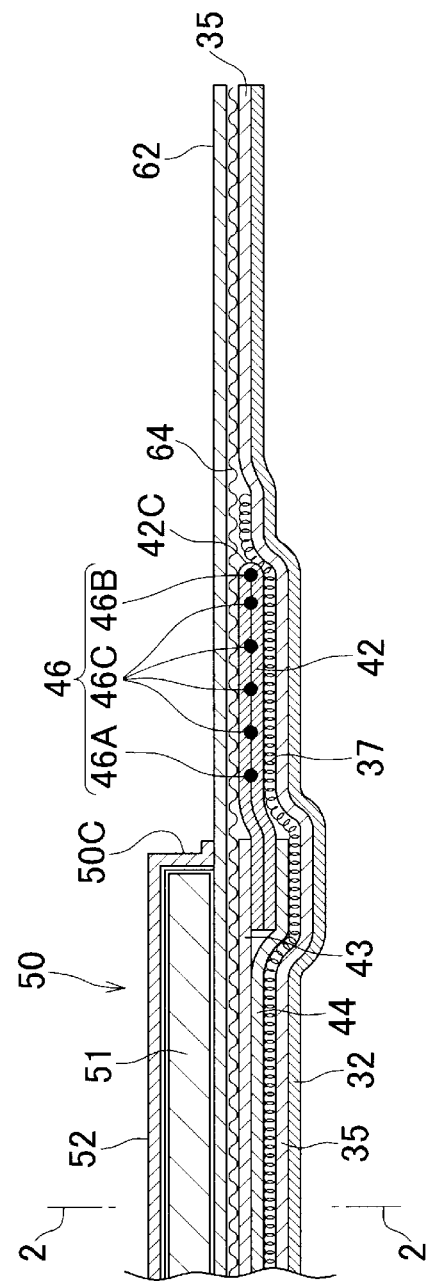
FIG. 6 is a scale-enlarged sectional view taken along line VI-VI in FIG. 2.

Referring to FIGS. 2, 4 and 6, a cover sheet 62 covering the rear end 40B may be joined to the interior crotch sheet 43 of the crotch panel 40 through a second joint region 64 formed of for example a hot melt adhesive. While only the rear waist panel 30 is illustrated in FIG. 6, in the front waist panel 20 also, a cover sheet 61 covering the front end 40A of the crotch panel 40 may be bonded to the interior crotch sheet 43 of the crotch panel 40 through a second joint region 63 (See FIG. 4). As material of the cover sheets 61, 62, for example, an SMS fibrous nonwoven fabric or a spun bonded fibrous nonwoven fabric each having a mass per unit area in a range of about 10 to about 30 g/m² may be used. The cover sheets 61, 62 may extend outwardly in the transverse direction X beyond the first joint regions 27, 37 and, according to at least one embodiment, the respective cover sheets 61, 62 have approximately the same dimension in the transverse direction X as that in the transverse direction X of the exterior waist sheet 32 and extend outwardly in the transverse direction X beyond the first joint regions 27, 37. The cover sheets 61, 62 are capable of preventing the hot melt adhesive of the first joint regions 27, 37 from adhering to the wearers skin, thereby protecting the wearer's skin from skin problems. The adhesives for the cover sheets 61, 62 are distributed inboard of the front and rear ends and the lateral edges of these cover sheets 61, 62 so that, when the cover sheets 61, 62 are joined to the interior crotch sheet 43, the adhesive is unlikely to run over these front and rear ends and the lateral edges.

In the diaper 1 as has been described hereinbefore, the first joint regions 27, 37 may be formed to extend beyond the outer lateral edge portions 42C of the respective leg sheets 42 and, in consequence, the outer lateral edge portions 42C are reliably joined to the front and rear waist panels 20, 30. Consequently, in the course of putting the wearer's legs through the leg-openings 17 of the diaper 1 and/or during use of the diaper 1, the outer lateral edge portions 42C is unlikely to be curled up inwardly of the diaper 1 and a desired fit is unlikely to be deteriorated. In addition, the outer lateral edge portions 42C may be respectively disposed with the outermost leg elastics 46B and the contractile force of the respective outermost leg elastics 46B facilitates the diaper 1 to be kept in close contact with the wearer's skin. Were the outer lateral edge portions 42C to be disposed with the elastics but these elastics not joined to the front and rear waist panels 20, 30, the outer lateral edge portions 42C would be further readily curled up inwardly of the diaper 1. In contrast, such situation may be reliably avoided according to some embodiments of the present invention as described herein.

In the respective leg sheets 42, the innermost leg elastic 46A may have a tensile stress higher than those of the outermost leg elastic 46B and the intermediate leg elastics 46C and consequently the crotch panel 40 may be put in close contact with the wearer's body in regions adjacent the absorbent structure 50 and prevent leakage of body exudates. A tensile stress of the respective outermost leg elastics 46B and the intermediate leg elastics 46C may be set to be relatively low and, in consequence, the leg sheets 42 may be prevented from being tucked inwardly and whereby the leg sheets 42 may be put in close contact with the wearer's groins.

A hot melt adhesive may be distributed on generally entire surfaces of the cover sheets 61, 62 facing to the interior crotch sheet 43 to form the second joint regions 63, 64 so that the adhesives overlap with each other in portions where the second joint regions 63, 64 directly overlap with the first joint regions 27, 37, and a stiffness is enhanced in these portions. The stiffness enhanced in this manner further reliably prevents the outer lateral edge portions 42C from being tucked inwardly. In addition, when the third and fourth waist elastics 26, 36 intersect with the respective outermost leg elastics 46B lying on the respective outer lateral edge portions 42C, the outer lateral edge portions 42C including the respective outermost leg elastics 46B are pulled outwardly in the transverse direction X under contraction of the third and fourth waist elastics 26, 36. Consequently, the outer lateral edge portions 42C are prevented from being tucked inwardly.

While both of the first joint regions 27, 37 lying in the front and rear waist panels 20, 30 are respectively located so as to overlap with the outer lateral edge portions 42C of the respective leg sheets 42 according to at least one embodiment, one or more of the described effect may be achieved also when at least the first joint region 37 in the rear waist panel 30 overlaps with the outer lateral edge portions 42C since the outer lateral edge portions 42C of the rear waist panel 30 adapted to come in contact with the wearer's buttocks are apt to be tucked inwardly during use of the diaper 1. While the first joint regions 27, 37 extend outwardly in the transverse direction X beyond the lateral edge portions 42C according to at least one embodiment, in further embodiments, the first joint regions 27, 37 do not extend outwardly beyond the lateral edge portions 42C so long as the first joint regions 27, 37 overlap with the outer lateral edge portions 42C.

While the cover sheets 61, 62 respectively extend between the lateral edge portions 20C, 30C of the front and rear waist panels 20, 30 according to at least one embodiment, in further embodiments, the cover sheets 61, 62 do not to fully extend between the lateral edge portions 20C, 30C so long as the cover sheets 61, 62 may cover the first joint regions 27, 37. While the cover sheets 61, 62 are prepared separately of the inner and exterior waist sheets 21, 31 and 22, 32 according to at least one embodiment, the interior waist sheets 21, 31 may serve also as the cover sheets, for example, when the interior waist sheets 21, 31 are extended in the longitudinal direction Y so as to cover the first joint regions 27, 37. In a similar fashion, the exterior waist sheets 22, 32 may serve also as the cover sheets when the exterior waist sheets 22, 32 are extended in the longitudinal direction Y so as to cover the first joint regions 27, 37.

The constituent elements of the disposable diaper 1 are not limited to those described in the present description but other various types of materials widely used, or to be developed, in the relevant technical field may be used without limitation unless otherwise stated. The terms "first", "second", "third" and "fourth" used herein are merely to distinguish the similar elements and/or similar positions.

The disclosure described above may be arranged in at least one or more of the following features:

A wearing article 1 having a longitudinal direction Y in parallel to a longitudinal axis 2-2, a transverse direction X in parallel to a transverse axis 3-3, a skin-facing surface, and a non-skin-facing surface lying on a side opposite to the skin-facing surface, including:

front and rear waist panels 20, 30 respectively defining front and rear waist regions 12, 13;

a crotch panel 40 defining a crotch region 14; and an absorbent structure 50 lying at least on the crotch panel 40, wherein:

the crotch panel 40 has front and rear end portions 40A, 40B extending in the transverse direction X and lateral edge portions 40C extending in the longitudinal direction Y, wherein the front and rear end portions 40A, 40B are joined to the front and rear waist panels 20, 30 through first joint regions 27, 37, and at least the first joint region 37 in the rear waist panel 30 overlaps with the lateral edge portions 40C of the crotch panel 40; and a cover sheet 62 covering the rear end portion 40B and the corresponding first joint regions 37 in the crotch panel 40 is attached to the rear waist panel 30.

The present disclosure may include at least the following embodiments, which may be taken in isolation or in combination with one another:

(1) Leg elastics 46 extending in the longitudinal direction Y are contractibly attached under tension to regions extending outwardly in the transverse direction X from the absorbent structure 50 of the crotch panel 40, and the leg elastics 46 overlap with the first joint regions 27, 37.

(2) At least portions of the leg elastics 46 are arranged along the lateral edge portions 40C of the crotch panel 40.

(3) The leg elastics 46 are spaced apart from each other in the transverse direction X, and the innermost leg elastic 46A as viewed in the transverse direction X has a tensile stress higher than that of the other leg elastics 46 lying outboard of the innermost leg elastic 46A as viewed in the transverse direction X.

(4) The cover sheet 62 extends outwardly in the transverse direction X beyond the lateral edges 40C of the crotch panel 40.

(5) The first joint regions 27, 37 extend outwardly in the transverse direction X beyond the lateral edges 40C of the crotch panel 40, and the lateral edges 40C lie inboard of lateral edges of the cover sheet 62.

(6) The crotch panel 40 includes a base sheet 41 and leg sheets 42 attached to both sides of the base sheet, and the leg sheets 42 extend outwardly in the transverse direction X beyond the absorbent structure 50.

(7) The cover sheet 62 is joined to the rear waist panel 30 through a second joint region 64, and the first joint region 37 and the second joint region 64 directly overlap with each other at least partially.

(8) Each of the leg sheets 42 has the outer lateral edge portion 42C folded inwardly in the transverse direction X to form a folding portion 45, the leg elastics 46 are attached within a sleeve defined by the folding portion 45, the outer lateral edge portion 42C, which is a portion of the leg elastics 46 lying outboard of the innermost leg elastics 46B, is folded inwardly along an outermost leg elastic 46B so that the outermost leg elastic 46B is located along an inside of the sleeve.

(9) The front and rear waist panels 20, 30 respectively include exterior waist sheets 22, 32 and interior waist sheets 21, 31, extension regions 22B, 32B of the exterior waist sheets 22, 32 extending from the interior waist sheets 21, 31 inwardly in the longitudinal direction Y;

the extension regions 22B, 32B are respectively disposed with reinforcing sheets 25, 35; and a plurality of waist elastics are respectively attached between the reinforcing sheets 25, 35 and the extension regions 22B, 32B in lateral portions of the reinforcing sheets 25, 35 and extension regions 22B, 32B.

(10) A plurality of waist elastics respectively intersect with at least the outermost leg elastic 46B.

(11) The exterior waist sheets 22, 32 respectively have folded regions 22A, 32A defined by portions of the exterior waist sheets 22, 32 extending outwardly in the longitudinal direction Y beyond outer end portions of the interior waist sheets 21, 31 and folded inwardly in the longitudinal direction Y, and a plurality of waist elastics are attached within the folded regions 22A, 32A.

(12) The wearing article has a longitudinal direction Y in parallel to a longitudinal axis 2-2, a transverse direction X in parallel to a transverse axis 3-3, a skin-facing surface and a non-skin-facing surface opposite to the skin-facing surface and includes a front waist region 12, a rear waist region 13, a crotch region 14 lying between the front and rear waist regions 12, 13, elastic front and rear waist panels 20, 30 respectively defining the front and rear waist regions 12, 13, a crotch panel 40 defining the crotch region 14 and attached to the respective skin-facing surfaces of the front and rear waist panels 20, 30 and an absorbent structure 50 located on the interior side of the crotch panel 40 so as to extend in the longitudinal direction Y.

(13) The front and rear waist panels 20, 30 are respectively defined by inner ends 20A, 30A, outer ends 20B, 30B and lateral edge portions 20C, 30C. The lateral edges 20C and the lateral edges 30C are overlapped with and joined to each other along a pair of series of seams 15 arranged at intervals in the longitudinal direction Y to form an annular elastic waist panel, thereby defining a waist-opening 16 and a pair of leg-openings 17.

(14) The front and rear waist panels 20, 30 respectively have interior waist sheets 21, 31 lying on the side of the skin-facing surface and exterior waist sheets 22, 32 lying on the side of the non-skin-facing surface. The exterior waist sheets 22, 32 have a width dimension in the longitudinal direction Y larger than those of the interior waist sheets 21, 31 and extend outwardly in the longitudinal direction Y beyond inner and outer ends of the interior waist sheets 21, 31.

(15) The exterior waist sheets 22, 32 have folded regions 22A, 32A defined by portions of the exterior waist sheets 22, 32 extending outwardly in the longitudinal direction Y beyond the outer ends of the interior waist sheets 21, 31 and folded inwardly in the longitudinal direction Y, and extension regions 22B 32B extending from the inner ends of the interior waist sheets 21, 31 toward the transverse axis 3-3. Within the folded regions 22A, 32A, a plurality of thread, strand or string first and second waist elastics 24, 34 are contractibly attached under tension. The first and second waist elastics 24, 34 extend in the transverse direction X across the entire regions 22A, 32A.

(16) The extension regions 22B, 32B of the exterior waist sheets 22, 32 extending from the interior waist sheets 21, 31 toward the transverse axis 3-3 are disposed with elongate reinforcing sheets 25, 35 formed of a fibrous nonwoven fabric and thread, strand or string third and fourth waist elastics 26, 36 are contractibly attached under tension respectively between the reinforcing sheets 25, 35 and the extension regions 22B, 32B. Both the third and fourth waist elastics 26, 36 are not continuous in vicinities of the longitudinal axis 2-2 so as to form inelastic regions 37A, 37B of respective mid sections 37A, 37B of the front and rear sections 12, 13.

(17) Between the respective interior waist sheets 21, 31 and the respective exterior waist sheets 22, 32, graphic display films 23, 33 formed of a plastic material are interposed so that these graphic display films may be respectively located on midsections in the transverse direction X of the front and rear waist regions 12, 13. The graphic display films 23, 33 may be printed on the surface facing the exterior waist sheets 22, 32 with graphics (not shown) or the like which are visually recognizable through the exterior waist sheets 22, 32.

(18) The crotch panel 40 has front and rear end portions 40A, 40B extending in the transverse direction X and overlapping with the front and rear waist panels 20, 30, and lateral edge portions 40C extending in the longitudinal direction Y and includes a base sheet 41 lying in a midsection in the transverse direction X and a pair of leg sheets 42 attached to lateral edge portions of the base sheet 41. The front and rear end portions 40A, 40B are defined by respective front and rear ends of the base sheet 41 and the leg sheets 42, respectively, and the lateral edge portions 40C are defined by respective outer lateral edge portions 42C of the leg sheets 42.

(19) The dimension in the longitudinal direction Y of the crotch panel 40 is smaller than the dimension in the longitudinal direction Y of the absorbent structure 50 and front and rear end portions 50A, 50B of the absorbent structure 50 lie outboard of the front and rear end portions 40A, 40B of the crotch panel 40 in the longitudinal direction Y.

(20) The base sheet 41 is composed of an interior crotch sheet 43 and an exterior crotch sheet 44. The leg sheets 42 have respective inner lateral edges attached between the interior and exterior crotch sheets 43, 44.

(21) Each of the leg sheets 42 has the outer edge portion 42C folded inwardly in the transverse direction X so as to form a folding portion 45, and a plurality of thread, strand or string leg elastics 46 extending in the longitudinal direction Y are attached within a sleeve defined by the folding portion 45. Thus the leg sheets 42 are elasticized with the leg elastics 46.

(21) The leg elastics 46 include an innermost leg elastic 46A closest to the longitudinal axis 2-2, i.e., lying on the innermost side in the transverse direction X, an outermost leg elastic 46B lying on the outermost side in the transverse direction X and intermediate leg elastics 46C lying between the innermost elastic 46A and the outermost elastic 46B.

(22) Single elastic threads are respectively used as the innermost leg elastic 46 and the outermost leg elastic 46B, and four threads are used as the intermediate leg elastics 46C.

(23) The outermost leg elastic 46B extends across the outer lateral edge portion 42C of the associated leg sheet 42 and the outer lateral edge portion 42C is folded inwardly along the outermost elastic 46B.

(24) The innermost leg elastic 46A has a tensile stress higher than those of the outermost leg elastic 46B and the intermediate elastics 46C.

(25) In the front waist panel 20, the third waist elastics 26 extending in the transverse direction X intersect with all of the innermost leg elastics 46, the outermost leg elastics 46B and the intermediate leg elastics 46C.

(26) In the rear waist panel 30, the fourth waist elastics 36 extending in the transverse direction X intersect with respective portions of the outermost leg elastics 46B and the intermediate leg elastics 46C but not with the remaining portions of the intermediate leg elastics 46C and the innermost elastics 46A.

(27) The absorbent structure 50 has a longitudinally long pad-like configuration and includes the front and rear ends 50A, 50B, lateral edges 50C, an absorbent core 51 extending in the longitudinal direction Y at least in the crotch region 14 and a bodyside liner 52 lying on an absorbent surface of the absorbent core 51. The front end 50A is attached to the interior waist sheet 21 of the front waist panel. The rear end 50B is attached between the interior waist sheet 31 of the rear waist panel 30 and the exterior waist sheet 32, more specifically, between the interior waist sheet 31 and the reinforcing sheet 35. An intermediate portion between the front and rear ends 50A, 50B is attached to the interior crotch sheet 43 of the crotch panel 40. The front end 50A of the absorbent structure 50 is attached to the surface of the interior waist sheet 21. The rear end 50B is attached between the interior waist sheet 31 and the exterior waist sheet 32.

(28) The front and rear ends 50A, 50B of the absorbent structure 50 lie outboard of the front and rear ends of the respective leg sheets 42 in the longitudinal direction Y.

(29) In portions of the front and rear ends 40A, 40B of the crotch panel 40, first joint regions 27, 37 extending in the transverse direction X from the base sheet 41 to the leg sheets 42 and the crotch panel 40 are joined to the front and rear waist panels 20, 30 through the first joint regions 27, 37.

(30) The first joint regions 27, 37 are formed of a hot melt adhesive distributed on the reinforcing sheets 25, 35 and lateral edge portions 27C, 37C extend outwardly in the transverse direction X beyond the outer lateral edge portions 42C of the respective leg sheets 42.

(31) The cover sheet 62 adapted to cover the rear end 40B is joined to the interior crotch sheet 43 of the crotch panel 40 through a second joint region 64.

(32) In the front waist panel 20, a cover sheet 61 adapted to cover the front end 40A of the crotch panel 40 is bonded to the interior crotch sheet 43 of the crotch panel 40 through a second joint region 63.

(33) The cover sheets 61, 62 extend outwardly in the transverse direction X beyond the first joint regions 27, 37, the respective cover sheets 61, 62 have approximately the same dimension in the transverse direction X as that in the transverse direction X of the exterior waist sheet 32 and extend outwardly in the transverse direction X beyond the first joint regions 27, 37.

(34) A hot melt adhesive is distributed on generally entire surfaces of the cover sheets 61, 62 facing to the interior crotch sheet 43 to form the second joint regions 63, 64 so that the adhesives overlap with each other in portions directly overlapping with the first joint regions 27, 37.

In the wearing article according to some embodiments of the present invention, the lateral edge portions of the crotch panel are joined to the rear waist panel through the first joint regions at least in the rear waist region and no dry edge is formed along the lateral edge portions. Consequently, these lateral edge portions are unlikely to be curled inwardly of the wearing article and these lateral edge portions may be kept in close contact with the wearer's body. Since the cover sheet overlapping with the first joint regions is attached to the rear waist panel, even if an adhesive defining the first joint regions extends outwardly in the transverse direction beyond the lateral edge portions, it is possible to prevent the adhesive from adhering to the wearer's skin and causing skin troubles.

Embodiments of the present invention are applicable to, for example, pants-type disposable diapers, disposable toilet-training pants and disposable incontinent pants.

This application claims the benefit of Japanese Application No. 2012-143515 the entire disclosure of which is incorporated by reference herein.

The invention claimed is:
1. A wearing article, comprising:
a longitudinal direction parallel to a longitudinal axis,
a transverse direction parallel to a transverse axis,
a skin-facing surface,
a non-skin-facing surface opposite to the skin-facing surface, front and rear waist panels respectively defining front and rear waist regions;
a crotch panel defining a crotch region; and
an absorbent structure lying at least on the crotch panel, wherein
the crotch panel has
front and rear end portions extending in the transverse direction, and
lateral edge portions extending in the longitudinal direction, wherein the front and rear end portions are joined to the front and rear waist panels through first joint regions, and at least the first joint region in the rear waist panel overlaps with the lateral edge portions of the crotch panel,
a cover sheet is positioned on a non-skin-facing surface of the absorbent structure, covers the rear end portion and the corresponding first joint region in the crotch panel, and is attached to the rear waist panel,
the crotch panel includes a base sheet and leg sheets attached to two lateral sides of the base sheet,
the leg sheets extend outwardly in the transverse direction beyond the absorbent structure,
each of the leg sheets has an outer lateral edge portion folded inwardly in the transverse direction to form a folding portion,
leg elastics are attached within a sleeve defined by the folding portion, and
the outer lateral edge portion is folded inwardly along an outermost leg elastic among the leg elastics so that the outermost leg elastic is located inside the sleeve.

2. The wearing article according to claim 1, wherein
the leg elastics extend in the longitudinal direction and are contractibly attached under tension to lateral regions of the crotch panel, the lateral regions extending outwardly in the transverse direction from the absorbent structure, and
wherein the legs elastics overlap with the first joint regions.

3. The wearing article according to claim 2, wherein at least some of the leg elastics are arranged along the lateral edge portions of the crotch panel.

4. The wearing article according to claim 2, wherein
at each of said lateral regions,
the leg elastics attached to said lateral region are spaced apart from each other in the transverse direction, and
among the leg elastics attached to said lateral region, an innermost leg elastic as viewed in the transverse direction has a tensile stress higher than that of the other leg elastics lying outboard of the innermost leg elastic as viewed in the transverse direction.

5. The wearing article according to claim 2, wherein the front and rear waist panels include a plurality of waist elastics intersecting with at least an outermost leg elastic among the leg elastics.

6. The wearing article according to claim 1, wherein the cover sheet extends outwardly in the transverse direction beyond the lateral edge portions of the crotch panel.

7. The wearing article according to claim 5, wherein
the first joint regions extend outwardly in the transverse direction beyond the lateral edge portions of the crotch panel, and
the first joint region in the rear waist panel has lateral edges lying inboard of lateral edges of the cover sheet.

8. The wearing article according to claim 1, wherein
the cover sheet is joined to the rear waist panel through a second joint region, and
the first joint region in the rear waist panel and the second joint region directly overlap with each other at least partially in a thickness direction of the wearing article.

9. The wearing article according to claim 1, wherein
the front and rear waist panels respectively include exterior waist sheets, interior waist sheets, reinforcing sheets, and a plurality of waist elastics,
the exterior waist sheets include extension regions extending in the longitudinal direction inwardly of inner edges of the interior waist sheets,
the reinforcing sheets are provided in the extension regions, and
the plurality of waist elastics are respectively attached between the reinforcing sheets and the extension regions in lateral portions of the reinforcing sheets and the extension regions.

10. The wearing article according to claim 1, wherein
the front and rear waist panels respectively include exterior waist sheets, interior waist sheets, and a plurality of waist elastics,
the exterior waist sheets respectively have folded regions defined by portions of the exterior waist sheets extending outwardly in the longitudinal direction beyond outer end portions of the interior waist sheets and folded inwardly in the longitudinal direction, and
the plurality of waist elastics are attached within the folded regions.

11. A wearing article, comprising:
a longitudinal direction parallel to a longitudinal axis,
a transverse direction parallel to a transverse axis,
a skin-facing surface,
a non-skin-facing surface opposite to the skin-facing surface,
front and rear waist panels respectively defining front and rear waist regions;
a crotch panel defining a crotch region; and
an absorbent structure lying at least on the crotch panel, wherein
the crotch panel has
front and rear end portions extending in the transverse direction, and
lateral edge portions extending in the longitudinal direction, wherein the front and rear end portions are joined to the front and rear waist panels through first joint regions, and at least the first joint region in the rear waist panel overlaps with the lateral edge portions of the crotch panel,
a cover sheet is positioned on a non-skin-facing surface of the absorbent structure, covers the rear end portion and the corresponding first joint region in the crotch panel, and is attached to the rear waist panel,
each of the front and rear waist panels includes an exterior waist sheet, an interior waist sheet, a reinforcing sheet, and a plurality of waist elastics,
the interior waist sheet has transversely extending inner and outer edges, the inner edge being closer to the transverse axis of the article than the outer edge,
the exterior waist sheet has an extension region extending longitudinally inward of the inner edge of the interior waist sheet, and
the plurality of waist elastics is attached between the reinforcing sheet and the extension region of the exterior waist sheet.

12. A wearing article having a longitudinal direction parallel to a longitudinal axis, a transverse direction parallel to a transverse axis, a skin-facing surface, and a non-skinfacing surface lying on a side opposite to the skin-facing surface, the article comprising:
> front and rear waist panels respectively defining front and rear waist regions;
> a crotch panel defining a crotch region; and
> an absorbent structure lying at least on the crotch panel, wherein
>> the crotch panel has
>>> front and rear end portions extending in the transverse direction and
>>> lateral edge portions extending in the longitudinal direction, wherein the front and rear end portions are joined to the front and rear waist panels through first joint regions, and at least the first joint region in the rear waist panel overlaps with the lateral edge portions of the crotch panel,
>> a cover sheet covering the rear end portion and the corresponding first joint region in the crotch panel is attached to the rear waist panel,
>> the front and rear waist panels respectively include exterior waist sheets, interior waist sheets, reinforcing sheets, and a plurality of waist elastics,
>> the exterior waist sheets include extension regions extending in the longitudinal direction inwardly of inner edges of the interior waist sheets,
>> the reinforcing sheets are provided in the extension regions, and
>> the plurality of waist elastics are respectively attached between the reinforcing sheets and
>> the extension regions in lateral portions of the reinforcing sheets and the extension regions.

13. A wearing article having a longitudinal direction parallel to a longitudinal axis, a transverse direction parallel to a transverse axis, a skin-facing surface, and a non-skin-facing surface lying on a side opposite to the skin-facing surface, the article comprising:
> front and rear waist panels respectively defining front and rear waist regions;
> a crotch panel defining a crotch region; and
> an absorbent structure lying at least on the crotch panel, wherein
>> the crotch panel has
>>> front and rear end portions extending in the transverse direction and
>>> lateral edge portions extending in the longitudinal direction, wherein the front and rear end portions are joined to the front and rear waist panels through first joint regions, and at least the first joint region in the rear waist panel overlaps with the lateral edge portions of the crotch panel,
>> a cover sheet covering the rear end portion and the corresponding first joint region in the crotch panel is attached to the rear waist panel,
>> the front and rear waist panels respectively include exterior waist sheets, interior waist sheets, reinforcing sheets, and a plurality of waist elastics,
>> the exterior waist sheets include extension regions extending in the longitudinal direction inwardly of inner edges of the interior waist sheets,
>> the reinforcing sheets are provided in the extension regions,
>> the exterior waist sheets respectively have folded regions defined by portions of the exterior waist sheets extending outwardly in the longitudinal direction beyond outer end portions of the interior waist sheets and folded inwardly in the longitudinal direction, and
>> the plurality of waist elastics are attached within the folded regions.

* * * * *